(12) United States Patent
Li

(10) Patent No.: US 10,758,282 B2
(45) Date of Patent: Sep. 1, 2020

(54) GENERAL ANATOMIC SELF-LOCKING PLATE FOR MEDIAL ACETABULUM AND AUXILIARY APPARATUS THEREOF

(71) Applicant: Ming Li, Zhejiang (CN)

(72) Inventor: Ming Li, Zhejiang (CN)

( * ) Notice: Subject to any disclaimer, the term of this patent is extended or adjusted under 35 U.S.C. 154(b) by 456 days.

(21) Appl. No.: 15/044,116

(22) Filed: Feb. 16, 2016

(65) Prior Publication Data

US 2017/0181784 A1 Jun. 29, 2017

(30) Foreign Application Priority Data

Dec. 25, 2015 (CN) .......................... 2015 1 0820287

(51) Int. Cl.
| | | |
|---|---|---|
| *A61B 17/80* | (2006.01) | |
| *A61B 17/17* | (2006.01) | |
| *A61B 17/84* | (2006.01) | |
| *A61B 17/88* | (2006.01) | |
| *A61B 17/90* | (2006.01) | |

(52) U.S. Cl.
CPC ...... *A61B 17/8066* (2013.01); *A61B 17/1728* (2013.01); *A61B 17/808* (2013.01); *A61B 17/842* (2013.01); *A61B 17/8875* (2013.01); *A61B 17/8057* (2013.01); *A61B 2017/90* (2013.01)

(58) Field of Classification Search
CPC .................... A61B 17/8061; A61B 17/8066
See application file for complete search history.

(56) References Cited

U.S. PATENT DOCUMENTS

| | | | | |
|---|---|---|---|---|
| 4,800,874 A | * | 1/1989 | David ............... | A61B 17/8061 606/286 |
| 6,306,173 B1 | * | 10/2001 | Masini ............... | A61B 17/8066 623/22.32 |
| 6,440,131 B1 | * | 8/2002 | Haidukewych .... | A61B 17/8061 606/286 |
| 2005/0165401 A1 | * | 7/2005 | Pack .................. | A61B 17/8066 606/281 |

* cited by examiner

Primary Examiner — Anu Ramana

(57) ABSTRACT

A general anatomic self-locking plate for medial acetabulum includes a left plate and a right plate mirrored with respect to the left plate. The right plate is a one-piece and includes a horizontal plate body and a vertical plate body. The horizontal plate body and the vertical plate body form a T shape. A through-hole is provided on the vertical plate body along a length direction thereof. Hole pathways of screw holes in the horizontal plate body lean downwardly along the free end of the horizontal plate body. The self-locking plate further includes stress bridges, automatic reduction holes and temporary positioning holes. An auxiliary apparatus of an anatomic self-locking plate for medial acetabulum includes a locking sleeve, a screw placing sleeve and a pair of gripping pliers. The right plate has excellent reduction and stable fixation, and is beneficial to accurately fix fractures without shaping and cutting during operation.

4 Claims, 10 Drawing Sheets

GENERAL ANATOMIC SELF-LOCKING PLATE FOR MEDIAL ACETABULUM AND AUXILIARY APPARATUS THEREOF

CROSS REFERENCE OF RELATED APPLICATION

The present invention claims priority under 35 U.S.C. 119(a-d) to CN201510820287.7, filed Dec. 25, 2015.

BACKGROUND OF THE PRESENT INVENTION

Field of Invention

The present invention relates to the field of plates in medical instruments, and more specifically, to a general anatomic self-locking plate for medial acetabulum and the auxiliary apparatus.

Description of Related Arts

A pelvis consists of an ilium, an ischium and a pubis. A big and deep fossa located in the outer lateral side of the pelvis is called acetabulum, and both the acetabulum and a caput femoris together make up a hip joint. The acetabulum is an important part of a hip joint. An acetabulum and adjacent structures can be divided into two parts, namely, the anterior column and the posterior column. The anterior column is also called ilium pubis column and it consists of anterior part of the ilium and superior part of the pubis, which starts from the anterior superior iliac spine, and goes through a rami ossis pubis, and then ends up at the symphysis ossium pubis. The posterior column presents a thick shape and can be called ilium ischium column as well, which includes the vertical part of the ischium and the posterior part of the ilium connected with the ischium and starts from the greater sciatic notch, goes through the center of the acetabulum, and ends up at the sciatic tuberosity. The anterior column and the posterior column together form an upside-down "Y" shape, like a cradle holding the acetabulum, and their inner lateral sides meet at a quadrilateral area, thereby avoiding the hip joint from moving inward. The iliac tuberosity at the outer side of the ilium goes down to a columnar area, where the acetabular dome is located and the bone mass there thickens. The inner bearing bone trabecula of the ilium distributes towards the acetabular dome and it is therefore called iliac dome line. The columnar shape along the direction of the iliac dome line can be called acetabular column. The anterior and posterior column meat at the angle of 60 degree and they form the shape of an arc, which is called acetabular dome and is a main weight-bearing area, supporting the articular surface of the hip joint. The purpose of operative treatment of acetabulum fractures is to recover the shape of normal concentric circles between the acetabulum and the hip joint.

The fractures happened at the acetabulum are mainly caused by high energy trauma. Currently, the commonly used fracture classification in clinic is Letournel-Judet, which divides the acetabulum fractures into 5 simple types and 5 complicated types. The type of the instability of displacement fractures needs an operative reduction and fixation. The surgical treatment must realize anatomical reduction and rigid internal fixation in order to ensure the functional exercise in the early stage, and to prevent severe complications, such as traumatic arthritis and osteonecrosis of the femoral head.

As the study of the metal property of implant materials is making a progress, the study of the imaging, the anatomy, the biology of the pelvis and acetabulum is deepening, and the study of the fracture mechanism of the pelvis and acetabulum is strengthening, it is widely accepted to take a skeleton bone model as the model object to do an operation. Anatomical reduction and stable fixation are the keys to deal with the instability of displacement fractures. For the fracture fixation around the quadrilateral area on the inner lateral sides of the acetabulum, the main problems are as follows: 1) two plates might be overlapped and fixed together, wherein the longitudinal plate is thinner and extends to the inner side of the acetabulum and therefore it doesn't work to fix comminuted fractures; moreover, since there are no locking sleeves, it is easy for screws to get into the joint or invade important vessels, nerves and organs around, and it thereby causes the secondary damage. The longitudinal plate is of a long-strip shape and thus likely to stab internal organs and vessels, especially to aged osteoporosis fractures. 2) The plates, screws, wires, steel needles used for pelvic and acetabular reconstruction are not stable enough, therefore some orthopaedic surgeons use two plates to form a "cross" in order to manually shape according to the different bone shapes of different patients during a model operation. As a result, it is not guaranteed during the operation to make the plates and the bone fit each other perfectly. During a model operation, shaping plates will prolong operation time, increase drug dosages, and cause more operation bleeding and different potential dangers. If two plates do not match well, for example, if some uneven sheer force and sliding displacement exist between the plates, the risk of reduction losing will increase, and consequently it is uncertain for the patient to restore the joint function at the early stage. In addition, lying in bed for a long period of time will also cause joint conglutination, muscle atrophy, partially losing joint function and etc. 3) When plates shape or bend repeatedly, nicks and scratches will leave on the surface of the plates, it will further cause more focal points of internal stress in the plates and accordingly cause implants to break more likely. 4) Shaping plates and matching bones unwell both will cause the fracture site to loosen, displace, pain and cause the stress shelter of the bones, and may further cause the fracture site to be nonunion or even malunion. 5) To the osteoporotic bone fractures around the quadrilateral area on the inner lateral sides of the acetabulum, there is no effective fixed instrumentation currently. The quadrilateral area of the acetabulum is adjacent to important structures such as internal and external iliac arteries and veins, femoral arteries and veins, obturator nerves, obturator arteries and veins, also adjacent to important organs such as intestinal canals, uterus, bladders. With little carelessness, those important structures or organs are very likely to be injured. Therefore, it is improper to strip and expose these structures during a model operation. Exposure is even more difficult to the fat patients; in order to leave a certain space and place the plates, it is needed to strip soft tissues, it however will cause bigger operation injury, e.g., more operation hemorrhage, longer anesthetic time, and longer operation time. 6) because it is pretty difficult to fix the fractures around the quadrilateral area on the inner lateral sides of the acetabulum, the incidence of complications is quite high, e.g., malreduction, unstable fixation, nonunion, malunion, slow union, traumatic arthritis, injuries of important vessels and nerves, breakage of internal implants, invalid or inefficient fixation, or failing operations. 7) There is a common weakness for the internal implant around the quadrilateral area on the inner lateral sides of acetabulum, that is inconformity with the transmission system of biomechanics of the pelvis and the acetabulum, i.e., the mechanics transmission route of the bone, which causes the stress transmission in the bone to disorder, generates negative effects on the fracture union, and it finally allows patients not to start the exercise at the early stage after the operation.

As the concept of "mini-invasive operation" is deepening in the modern orthopedics, it is required to make the surgery as small as possible in order to bring the best clinical effect. To the surgery involving the fractures around the quadrilateral area on the inside of the acetabulum, it is needed to take some anterior approach exposure, such as the modified Stoppa's approach, and ilioinguinal approach. Because the anatomic shape of the pelvis and the acetabulum is irregular, and there are lots of important vessels, nerves, organs and soft tissues around, many aspects are limited, e.g., the exposure range of the surgical incision, and the size and strength of the internal implant, which bring a huge difficulty and risk to the operative reduction and internal fixation. Thus, there is a strict requirement to the built-in materials and matching operating instrumentation.

The patent "Anatomical plate around the quadrilateral area of the pelvis and acetabulum", Chinese Patent No. 201020587890.5, discloses an anatomical plate, which comprises a shapable plate body with a bending shape; a plurality of locking holes are set in the plate body; a positioning structure is set in the plate body for treating the fracture displacement around the quadrilateral area, wherein a positioning baffle at the quadrilateral area is connected to the plate body for forming one piece structure so as to avoid problems existing in previous split plates; the locking holes set in the plate body are good for those patients with comminuted fractures or osteoporosis. However, the plate still has some disadvantages.

1) The positioning baffle around the quadrilateral area is of a U shape and no any locking holes are set therein, which is unable to effectively fix the smashed fracture fragments in a free state, or even fixable but not firm enough, thus it will cause higher incidence of complications such as the nonunion of model bone fractures, slow union or malunion, or traumatic arthritis, or injury of important vessels and nerves, breakage of internal implants, or invalid or inefficient fixation, or failing operation, and make the applicable range of the plates limited.

2) The plates need to be shaped manually during the operation according to different bone shapes of every patient. However, it is not guaranteed to fit the shaped plates in a model operation and the bone perfectly. In addition, shaping the plates in a model operation will lead to longer operation time, more anaesthetic dosage, more operative hemorrhage, and etc. Moreover, shaping or bending plates repeatedly will leave nicks and scratches on the surface of the plates, cause more focal points of internal stress in the plates, and accordingly cause implants to break more likely.

3) The quadrilateral area on the inside of the acetabulum is located in the pelvis, with a deep position, a difficult exposure and a complicated local structure, being adjacent to important structures such as uterus, ovaries, bladders, internal and external iliac arteries and veins, femoral arteries and veins, obturator nerves, obturator arteries and veins. During fixing the plates, it is easy for screws to get into the joint or damage important vessels, nerves and organs around, and causes the secondary damage. Therefore, the plate has lower safety and reduces the operative efficiency.

4) The inconformity with the transmission system of biomechanics of the pelvis and the acetabulum, i.e., the mechanics transmission route of the bone causes the stress transmission in the bone to disorder, generates negative effects on the fracture union, which finally allows patients not to start the exercise at the early stage after the operation.

5) The screws in the plate can't reach and fix the posterior wall of the acetabulum.

6) The baffle of the quadrilateral area of the plates is vertical to the plate body, which doesn't comply with the normal shape of the surface of the bones of the pelvis.

7) The baffle of the quadrilateral area of the plates doesn't comply with the normal shape of the surface of the bones of the acetabulum, because it just roughly shows the position of the quadrilateral area, but it doesn't actually fit the bone. The anterior and posterior edge of a normal acetabulum quadrilateral area have different torsion curvatures and radians, usually the difference being 10 degrees to 20 degrees, no matter for adults, children, for male or female.

8) There is no specific quantitative description with the plates to tell the specific angle and direction of the locking screw hole, but only roughly mentioning it with the locking hole. However, this should be one of the key processes in a model operation to internally fix the acetabulum fractures. If there is merely 3 degrees of error for a screw inserting, it might get into joints, or injure important vascular structures like obturator artery and vein, superior gluteal artery and vein, superior gluteal nurves.

SUMMARY OF THE PRESENT INVENTION

One objective of the present invention is to provide a general anatomic self-locking plate for medial acetabulum and an auxiliary apparatus thereof, which has good versatility, is safe and efficient, convenient to use, and good for precisely fixing acetabular fractures.

Accordingly, in order to accomplish the above objective, the present invention adopts a technical solution as follows. A general anatomic self-locking plate for medial acetabulum comprises a horizontal plate body and a vertical plate body, wherein: the horizontal plate body and the vertical plate body form a T shape;

the horizontal plate body comprises a first fixation zone, a second fixation zone, a third fixation zone, a fourth fixation zone and a fifth fixation zone connected with each other in sequence, and the vertical plate body is connected with the third fixation zone;

the vertical plate body comprises a sixth fixation zone, a seventh fixation zone, an eighth fixation zone, a ninth fixation zone and a tenth fixation zone, wherein: a through-hole is provided on the vertical plate body along a length direction thereof, provided between the sixth fixation zone and the seventh fixation zone and provided between the eighth fixation zone and the ninth fixation zone; the third fixation zone, the sixth fixation zone and the eighth fixation zone are connected with each other in sequence, the third fixation zone, the seventh fixation zone and the ninth fixation zone are connected with each other in sequence;

the tenth fixation zone is located at a free end of the vertical plate body for matching an anatomic shape of the medical acetabulum;

a first sliding slot is provided along a length direction of the third fixation zone, a second sliding slot is provided along a width direction of the tenth fixation zone, a portion of the third fixation zone at two sides of the first sliding slot defines a first stress bridge, a portion of the tenth fixation zone at two sides of the second sliding slot defines a sixth stress bridge; an arched junction of the horizontal plate body and the sixth fixation zone defines a second stress bridge; an arched junction of the horizontal plate body and the seventh fixation zone defines a third stress bridge;

the first, second, third, fourth, fifth, eighth, ninth and tenth fixation zones are all provided with locking screw holes; upper end surfaces of the screw holes in the horizontal plate body are closer to the third fixation zone than lower end surfaces thereof, upper end surfaces of the screw holes in the sixth and the seventh fixation zones are closer to the through-hole than lower end surfaces thereof;

a rim of the self-locking plate has a smooth shape.

To optimize the present invention, more measures are taken as follows:

An angle γ1 between a free end of the first fixation zone and the third fixation zone is in a range of 5°-18°. An angle γ2 between a free end of the fifth fixation zone and the third fixation zone is in a range of 0°-10°. An intersection angle E formed by a central axis of the vertical plate body and a central axis of the third fixation zone is in a range of 950-1050.

An angle α1 of the eighth fixation zone and the first fixation zone is in a range of 105°-120°. An angle β1 of a central axis of the eighth fixation zone and the third fixation zone is in a range of 105°-120°.

An angle α2 of the ninth fixation zone and the fifth fixation zone is in a range of 99°-105°. An angle β2 of a central axis of the ninth fixation zone and the third fixation zone is in a range of 90°-105°.

A length of the first sliding slot is in a range of 25.0 mm-50.0 mm, and a width thereof is in a range of 3.0 mm-8.0 mm. A length of the second sliding slot is in range of 3.0 mm-10.0 mm and a width thereof is in a range of 2.2 mm-3.5 mm.

An angle ω formed by a central axis of one of the screw holes and a normal line of an end surface of the one of the screw holes is in a range of 0°-20°.

A temporary positioning hole for using Kirschner wires is provided in the horizontal plate body of the self-locking plate. The sixth and the seventh fixation zone is provided with 1-2 automatic reset holes, respectively.

Fixed slots are set oppositely on an inner wall of every screw hole. A distribution of each screw hole in the right plate complies with a load sharing principle and neutral principle.

The first fixation zone is provided with a temporary positioning hole at an end thereof.

The screw holes on the first fixation zone are set in one or two rows, but the screw holes on the fifth fixation zone are set in one row.

The vertical plate body is provided with one to two screw holes at a place near the horizontal plate body, each being located at the sixth and the seventh fixation zone, respectively. There are 1-2 second sliding slots in the tenth fixation zone. The eighth and the ninth fixation zone is provided with a third sliding slot, respectively. The plate bodies of the eighth and ninth fixation zone at the two sides of the third sliding slot are taken as a fourth stress bridge and a fifth stress bridge.

The eighth and the ninth fixation zone each extends outward and forms a fixed arm which matches the anatomic shape of the medial acetabulum. Each fixed arm is provided with a screw hole and a fourth sliding slot. A length of the fourth sliding slot is 3.0 mm to 6.0 mm, a width thereof is 2.2 mm to 3.5 mm. The plate bodies of the eighth and the ninth fixation zone at the two sides of the fourth sliding slot are taken as a seventh stress bridge and an eighth stress bridge.

Another object of the present is to provide an auxiliary apparatus of the anatomic self-locking plate for medial acetabulum, which comprises a locking sleeve, a screw placing sleeve and a pair of gripping pliers, wherein the locking sleeve is provided with a first handle on a top thereof; the first handle is provided with skidproof grains on a periphery thereof and with positioning external threads at an end thereof, the positioning external threads are engaged with internal threads of the screw hole of the right plate fittingly for leading a drill to directionally drill in order to pre-drill a safe screw pathway; the locking sleeve is able to accommodate the drill matching a pore diameter of the screw pathway; a second handle is provided on a top of the screw placing sleeve, with skidproof grains set on a periphery thereof; the second handle has one to two fixing feet fittingly connected with the fixing slot of the right plate; an adjustable angle of the sleeve and the right plate is set between 00 to 25° in order to ensure that the screw can be screwed at a safe preset angle; the pair of gripping pliers comprises a gripping body with an end expanding to an annual gripping head, the annual gripping head being provided with skidproof grains inside.

Another object of the present invention is to provide a method for installing the anatomic self-locking plate for medial acetabulum.

When installing the plate, placing the first fixation zone on the upper rear part of the acetabulum, i.e., a block area where the arcuate line part of the posterior column of the acetabulum inside a pelvis extends backward to the sacroiliac joint, wherein the directions of the screw holes within the block area all point towards the posterior wall and posterior column area of the acetabulum, and making the area have a 70°-90° of inclining angle relative to the surface of the first fixation zone in order to prevent the screws from getting into the joint; then fixing the posterior wall and the posterior column area of the acetabulum; then fixing the rear half of the load bearing area on the acetabular dome with the screw holes of the second fixation zone.

Make the third fixation zone contacted with the part right above the acetabulum, fix the fractures in the fornix part right above the acetabular dome and the fractures in acetabular anterior wall, and insert Kirschner wires into the first sliding slot to fix the right plate initially to allow the right plate to adjust positions without slipping.

The screws in the fourth fixation zone point towards the anterior column and the anterior wall of the anterior lateral of the acetabulum, and have a 0°-20° of inclining angle relative to the surface of the fourth fixation zone in order to prevent screws from getting into the joint; then fixing the front half of the load bearing area on the acetabular dome.

Placing the fifth fixation zone above the anterior column of the acetabulum, i.e., above the superior ramus of pubis, wherein the screw directions in this block area have a 0°-10° of inclining angle with respect to the surface of the fifth fixation zone, decreasing in sequence by a 30-5° from the first hole adjacent to the third fixation zone, which is for preventing the screws from getting into the joint; then fixing the first half part of the loading bear area of the acetabular dome with the screw holes in the fourth fixation zone, and fixing the superior ramus of pubis of the anterior column of the acetabulum by using the remaining screw holes near the free end.

Bolt the eighth fixation zone to ½ of the upper-middle part of the posterior column of the acetabulum. Bolt the ninth fixation zone to ½ of the upper-middle of the anterior column of the acetabulum. Screw the tenth fixation zone to the lower-middle part of the quadrilateral area of the medial acetabulum.

The automatic reduction hole can make the fracture fragments which protrude to into a pelvic cavity a normal reduction, when inserting screws.

Compared with the prior arts, the present invention has the following advantages:

The right plate is able to match the anatomic shape of the medial acetabulum model, is good for the fracture reduction of the acetabulum model, has firm fixation, forms plural of lateral stress bridge, longitudinal stress bridge and the stress bridge of torsion and bending, the stress distributing evenly so that it can prevent the screws from loosening and breaking, reduce complications at the later stage of fractures, such as implants' loosening, displacement, pain and the stress shielding of bones, and accordingly it can benefit a precise fracture fixation.

The shaping or cutting is not needed during the model operation of the right plate, the model operation time is saved, the operation efficiency is increased, hemorrhage during the model operation, infection risk and the model operation risk are all decreased. At the same time, the right plate allows appropriate torsion in a three dimensional space in order to adapt an unusual bone model and increase the fitness of the right plate and the bone model.

Moreover, the present invention is applicable to the fractures in the quadrilateral area of medial acetabulum model, to the fractures related to the load bearing area on the acetabular dome, and with the fractures of anterior column of acetabulum or with the superior ramus fractures of pubis, and with the fractures of the anterior wall of acetabulum, and with the fractures of the posterior column of acetabulum, and with the posterior wall of acetabulum, to the artificial hip joint replacement surgery. The present invention is applicable to different patients with different ages, genders, bone sizes and shapes.

In addition, the pair of gripping pliers in the present invention can be used to hold the right plate, which prevents the surface of the right plate from being scratching and from falling into the wound when placing the plate during a surgery, and then ensures that the right bone place is placed in a right position and the position with no slipping when screws are being inserted inward. The skidproof grains set on the top of the pair of gripping pliers benefit holding the right plate, and the width of the pliers fits the width of the right plate.

DETAILED DESCRIPTION OF THE PREFERRED EMBODIMENT

Figure 1:
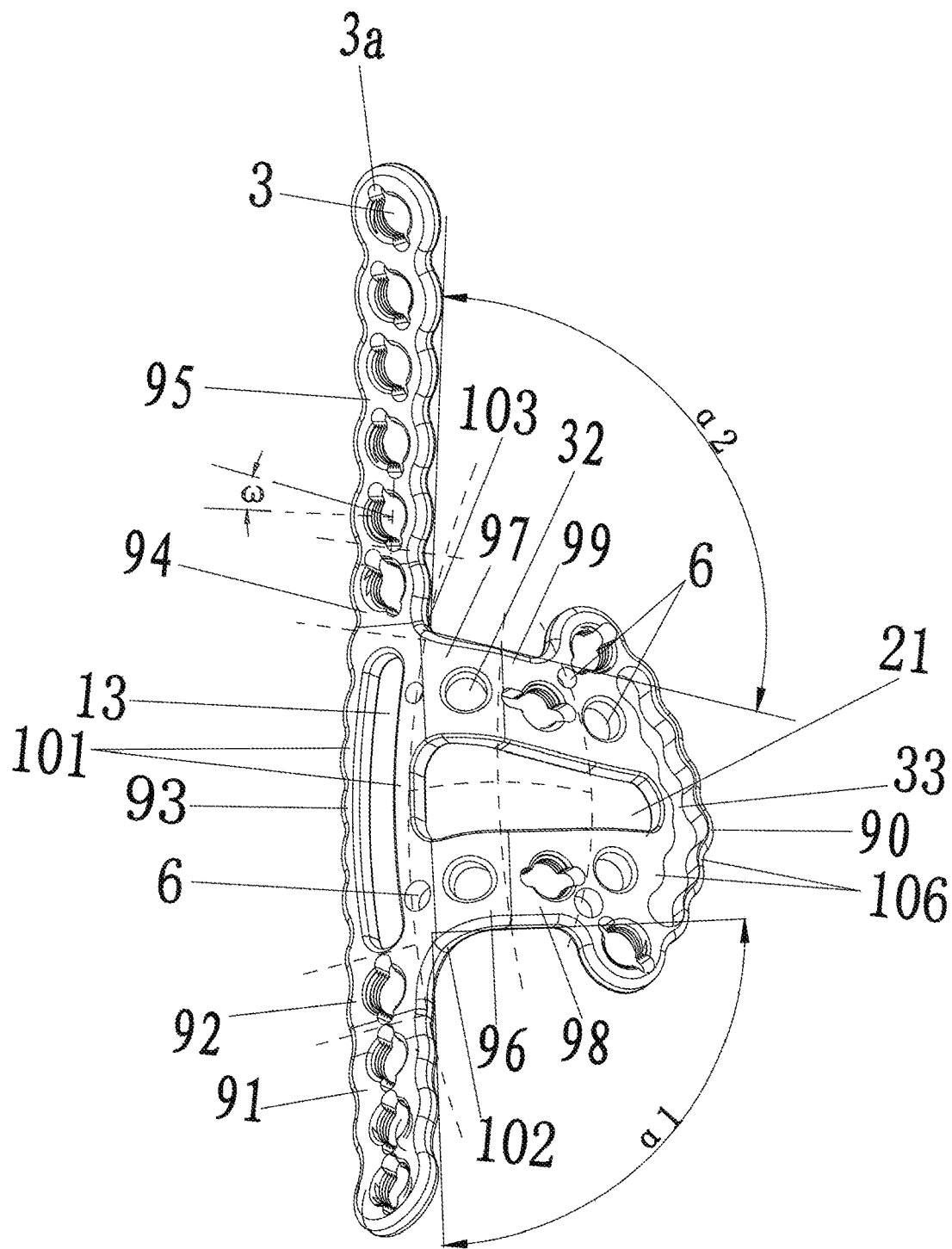
FIG. 1 is a schematic front view of the first embodiment of the present invention.
Figure 2:
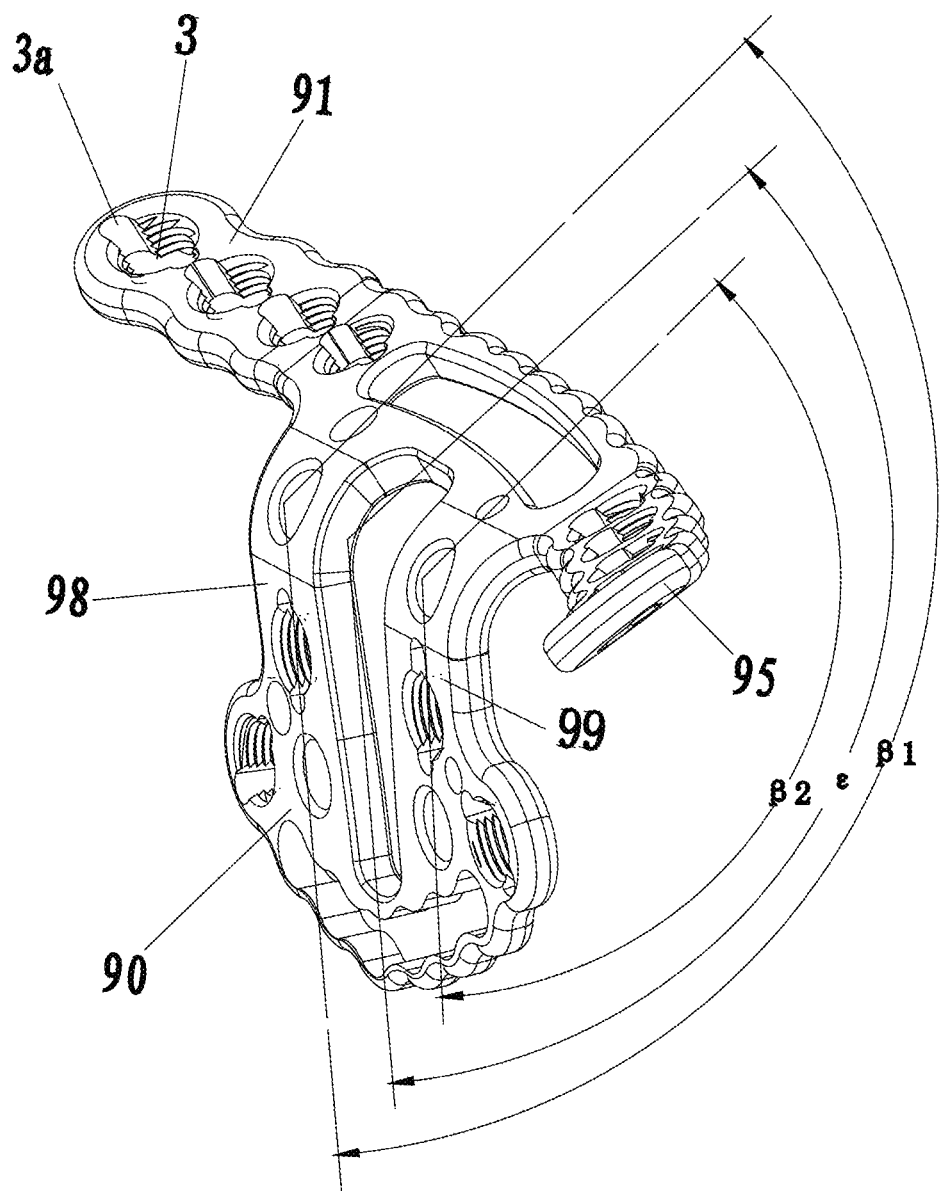
FIG. 2 is a schematic solid view of FIG. 1.
Figure 3:
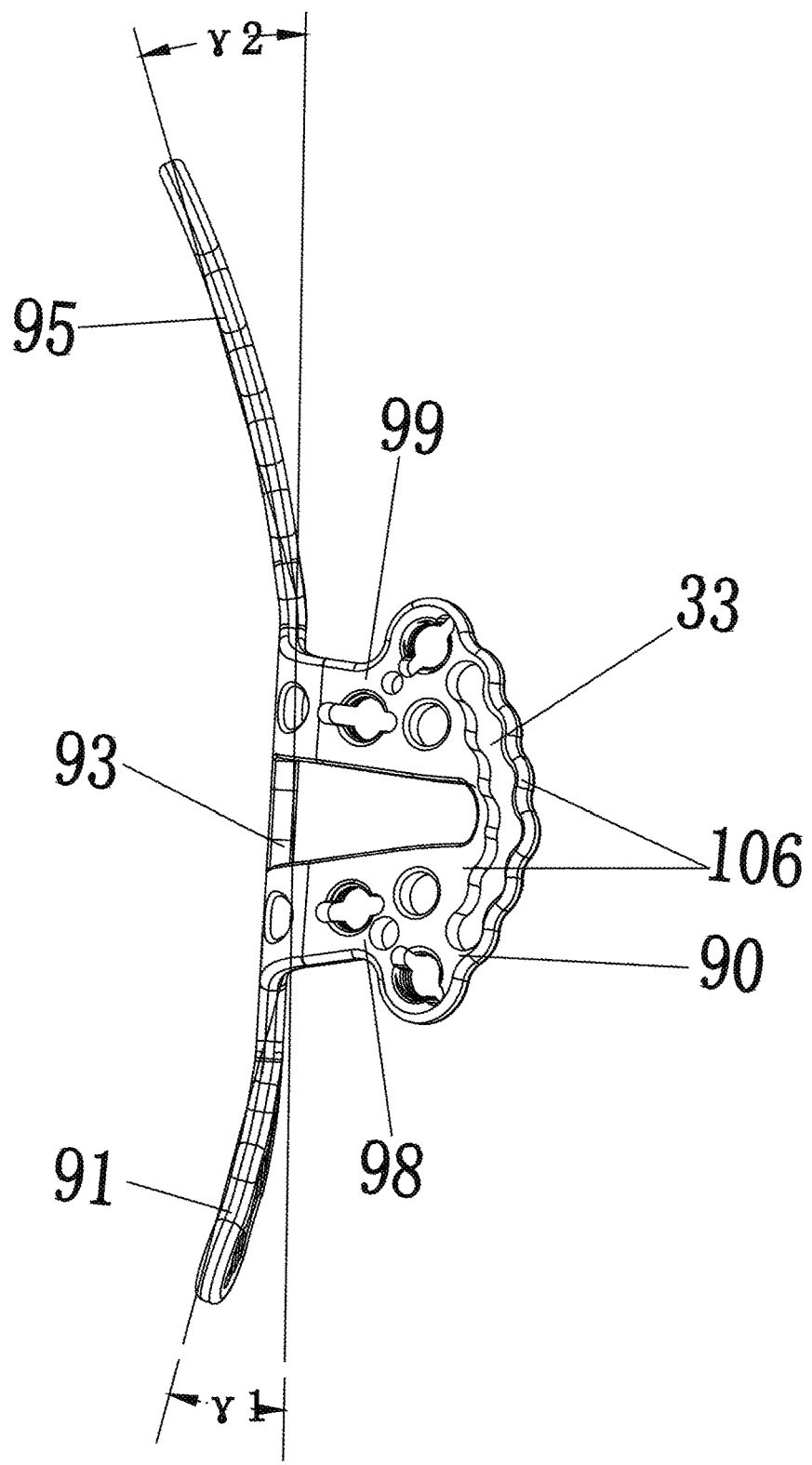
FIG. 3 is a schematic side view of the horizontal plate body in the first embodiment of the present invention.
Figure 4:
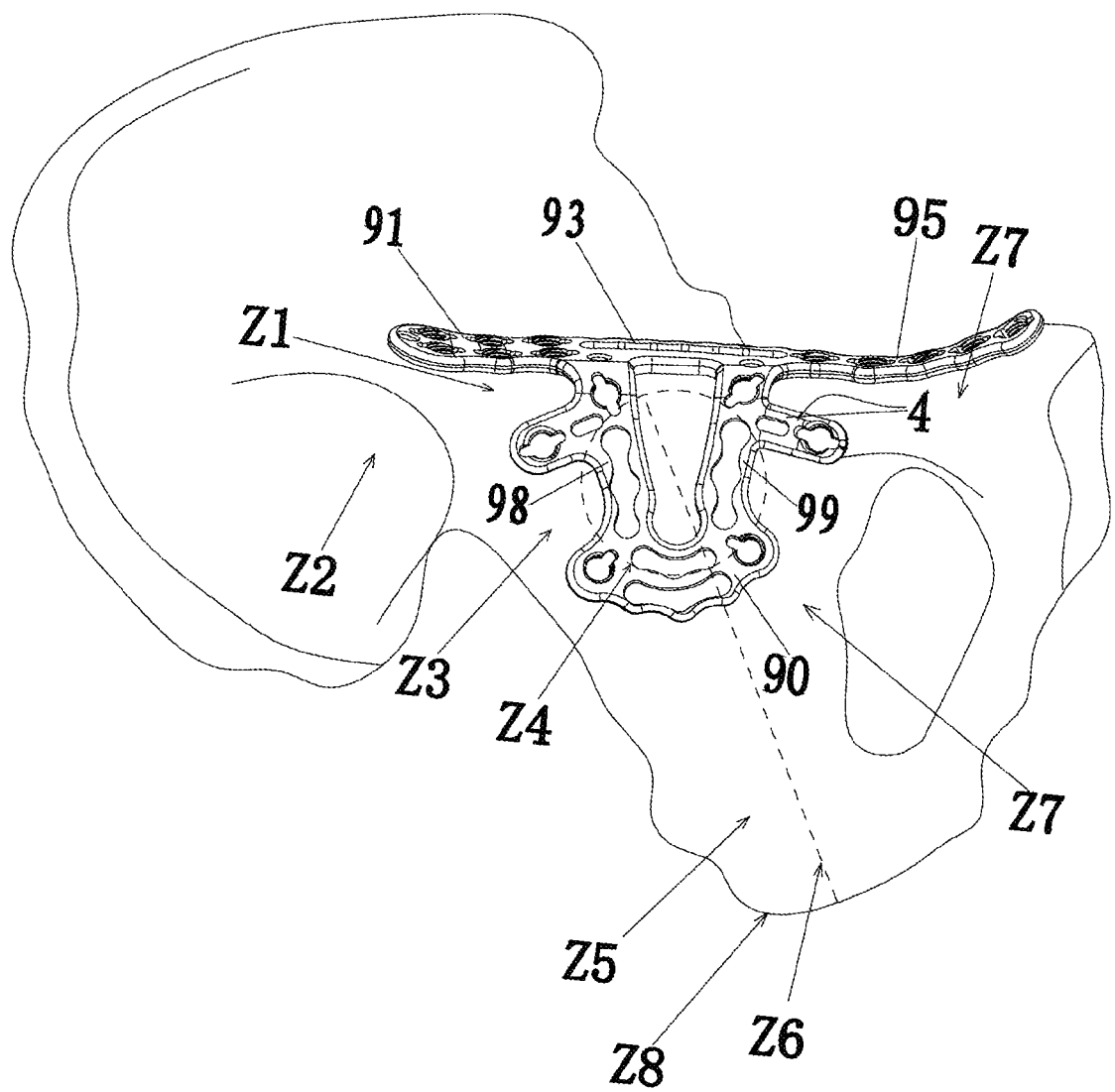
FIG. 4 is a schematic view of the use status of the right plate in fifth embodiment of the present invention.

The present invention is further described in detail accompanying with drawings and embodiments as follows.

FIGS. 1 to 11 are structurally schematic views of the present invention.

The reference numbers are explained as follows: 13—the first sliding slot; 21—through hole; 33—second sliding slot; 3—screw hole; 3a—fixing slot; 32—automatic reduction hole; 23—third sliding slot; 4—fixing arm; 41—the fourth sliding slot; 51—right finger circle; 51a—sawtooth bar; 53—left finger circle; 53a—stop bulge; 52—holding part; 52a—gripping head; 6—temporary positioning hole; 8—screw placing sleeve; 81—second handle; 82—fixing feet; 91—first fixation zone; 92—second fixation zone; 93—third fixation zone; 94—fourth fixation zone; 95—fifth fixation zone; 96—sixth fixation zone; 97—seventh fixation zone; 98—eighth fixation zone; 99—ninth fixation zone; 90—tenth fixation zone; 101—first stress bridge; 102—second stress bridge; 103—third stress bridge; 104—fourth stress bridge; 105—fifth stress bridge; 106—sixth stress bridge; 107—seventh stress bridge; 108—eighth stress bridge; Z1—the posterior column of acetabulum; Z2—acetabulum joint; Z3—lower half part of ischiadic ramus; Z4—projection zone of acetabulum joint; Z5—ramus of ischium; Z6—middle line of ischiadic ramus; Z7—superior ramus of pubis; Z8—ischiadic tuberosity; L1—central axis of hole pathway; L2—normal of end face of hole pathway.

As shown in drawings, a general anatomic self-locking plate for medical acetabulum of the present invention comprises a horizontal plate body and a vertical plate body, wherein the horizontal plate body and the vertical plate body form a T shape; the horizontal plate body fits a shape of acetabular dome, posterior and anterior column, and fits a superior ramus of pubis smoothly.

The horizontal plate body comprises a first fixation zone 91, a second fixation zone 92, a third fixation zone 93, a fourth fixation zone 94 and a fifth fixation zone 95 connected with each other in sequence. The vertical plate body is connected with the third fixation zone 93. The first fixation zone 91 fits a shape of a posterior wall and a posterior column of an acetabular rear smoothly. The fifth fixation zone 95 fits a shape of an anterior column and wall of an acetabular front smoothly. The third fixation zone 93 fits a shape of an anterior wall of an upper part of an acetabulum model smoothly and fixes fractures right above the acetabular dome.

The vertical plate body is provided with a through-hole 21 along a length direction thereof as a blood supply channel. A sixth fixation zone 96 and a seventh fixation zone 97, both being connected with the third fixation zone 93, are respectively formed at two sides of the through-hole 21. An eighth fixation zone 98 is connected with a lower end of the sixth fixation zone 96. A ninth fixation zone 99 is connected with a lower end of the seventh fixation zone 97.

A free end of the vertical plate body is a tenth fixation zone 90, which is formed by expanding along a plane of the vertical plate body and matches an anatomic shape of the medial acetabulum. The tenth fixation zone 90 is connected with the eighth fixation zone 98 and the ninth fixation zone 99, respectively. Each of the first, second, third, fourth, fifth, eighth, ninth and tenth fixation zone 91, 92, 93, 94, 95, 98, 99 and 90 is provided with a screw hole 3. The right plate is fixed to a hip bone through these screw holes 3. It takes a reinforced role to drive the screw into the second and the fourth fixation zone 92 and 94 in the situation with a thick hop bone, while it is no needed for a small hip bone.

Left and right arc-shaped junctions of the horizontal and the vertical plate body are taken as a second stress bridge 102 and a third stress bridge 103, respectively. The second stress bridge 102 complies with a distribution of a bone trabecula of an internal tension in a rear half part of the posterior column of the acetabulum. The third stress bridge 103 accords with a distribution of the bone trabecula of the internal tension in a front half part of the posterior column of the acetabulum. The stress tension structure is designed to conduct a force between adjacent zones uniformly and prevent the breakage of screws or plates.

A first sliding slot 13 is provided along a length direction of the third fixation zone 93. A second sliding slot 33 is provided along a width direction of the tenth fixation zone 90. The first sliding slot 13 and the second sliding slot 33 are as adapted for an initial fixation of Kirschner wires, thereby ensuring to position the right plate in a right place. The plate body at two sides of the first sliding slot 13 is taken as a first stress bridge for conducting the force from the rear part of the acetabulum to the front part, which complies with the distribution of the bone trabecula of the internal tension and distributes stress uniformly. The plate body at two sides of the second sliding slot 33 is taken as a sixth stress bridge 106, which complies with the distribution of the bone trabecula of the internal tension in the middle and lower part of the quadrilateral area, is convenient to conduct and disperse the stress above, prevents concentrated stress, and prevents inserted screws and steel plates from breaking.

The hole pathway of the screw holes 3 in the horizontal plate body lean toward the third fixation zone 93, wherein upper end surfaces of the hole pathway near the third fixation zone 93, lower end surfaces are far away from the third fixation zone 93. The hole pathways of the screw holes 3 in the sixth fixation zone 96 and the seventh fixation zone 97 lean toward the through-hole 21, wherein upper end surfaces of the hole pathways near the through-hole 21, lower end surfaces are far away from the through-hole 21. When a screw is driven into a hip bone along the preset inclining screw hole 3, the screw is prevented from penetrating the acetabulum, avoiding the acetabulum and the vessels or nerves around. While inserting screws into the screw holes 3 beside the first sliding slot 13 to match a thicker acetabulum, a reinforced fixation effect can be realized.

A rim of the horizontal and the tenth fixation zone 90 shows a wavy contour, wherein a rim of the right plate shows a smooth shape, and a junction part of the horizontal and the vertical plate body shows a smooth transition. The smooth rim can reduce damage to the pelvic organ and important vessels and nerves, and muscular tissues, and it is convenient for the soft tissues such as surrounding vessels to grow and cover it and to reconstruct blood supply; in addition, it can reduce the incidence rate of fracture nonunion, slow union or malunion, and reduce the dead space around the right plate; the smooth arc transition complies to the path of the biomechanic transmission of the acetabulum, complies with the surface shape of the acetabular dome, inside and front and rear part, complies with the characteristic of bone trabecula inside, hence the stress distributes evenly, being able to effectively disperse the stress at the fracture end, reduce the breakage risk of screws and the right plate, and being good for the right plate to bear loads. In short, it can benefit the union of the wound, increase the success rate of the internal fracture fixation in a model operation, and it can further reduce compression on pelvic organs, vessels and nerves, and soft tissues.

In the embodiment, in order to perfectly fit the horizontal plate body 1 with the surface of bones, a free end of the first fixation zone 91 inserts anticlockwise with respect to the third fixation zone 93 with a torsion angle $\gamma 1$ between 5°-18°. A free end of the fifth fixation zone 95 inserts clockwise with respect to the third fixation zone 93 with a torsion angle $\gamma 2$ between 0°-10°. An intersection angle c formed by a central axis of the vertical plate body and a central axis of the third fixation zone 93 is 95°-105°. A frontal intersection angle $\alpha 1$ of the eighth fixation zone 98 and the first fixation zone 91 is between 105°-120°. An intersection angle $\beta 1$ of a central axis of the eighth fixation zone 98 and the third fixation zone 93 connected with the eighth fixation zone 98 is 105°-120°. A frontal intersection angle $\alpha 2$ of the ninth fixation zone 99 and the fifth fixation zone 95 is between 99°-105°. An intersection angle $\beta 2$ of a central axis of the ninth fixation zone 99 and the third fixation zone 93 connected with the ninth fixation zone 99 is 90-105°. A length of the first sliding slot is 25.0 mm-50.0 mm, and a width thereof is 3.0 mm-8.0 mm. A length of the second sliding slot is 3.0 mm-10.0 mm and a width thereof is 2.2 mm-3.5 mm. An intersection angle $\omega$ formed by a central axis L1 of the hole pathway of a screw hole 3 and a normal line L2 of an end surface of the hole pathway is 0°-20°. The hole path of the locking screw hole 3 is preset with a safe direction, so that all directionally inserted screws can avoid the distributed design of the hip joint, the obturator nerves and vessels, and the superior gluteal nerves and vessels in the model of human body. The screw exits in a safe area. With respect to the front and back, the inside and outside, the top and bottom of the plate body, the screw hole presents an inclining angle of 0°-20°, evenly distributing around the hip joint model, which can ensure a safe angle of inserted screws.

In the embodiment, a temporary positioning hole 6 for using Kirschner wires is provided in the right plate. The sixth fixation zone 96 and the seventh fixation zone 97 are provided with 1-2 automatic reduction holes 32, respectively. According to the size of the plate, the automatic reduction hole 32 can use the temporary positioning hole 6 or the screw hole 3. An automatic reduction hole 32 with a inserted screw can automatically fix the plate to a normal acetabular anterior column and posterior column, press the fracture fragment in the internal quadrilateral area that gets into the pelvis and displaced back to the normal position, and therefore avoiding using dangerous operative instruments such as the acetabulum hook, supporting rob and so on. Since this area is rich in important structures, such as obturator arteries and veins, obturator nerves, ureter, spermatic cord, intestinal canal, bladders, uterus, ovaries, fallopian tube, any carelessness with theses sharp-headed reduction apparatuses like the hook and the supporting rob, for example, even a little placement deviation could cause accidental injuries and severe consequence. After placing a plate to a proper position, merely inserting a screw into the automatic reduction hole can entirely extrude the comminuted fracture fragments in the quadrilateral area outward and reduce through the fixation zone of plate B zone and C zone, e.g., to treat the central dislocation of the acetabulum with the fractures in the quadrilateral area, one-time fixing two parts can avoid using multiple plates, keep anatomical reduction, and prevent complications for internal fracture fixation, for example, reduction loss after surgery, sclerotin absorption of small pieces of bone, sclerotin defect and etc. Naturally, safe fixation can be realized, surgical risk of accidentally injuring normal tissues can be decreased, operative efficiency can be increased, operative steps of complicated reduction are reduced, operation time is lessened, and infection risk and incision hemorrhage are reduced.

Figure 5:
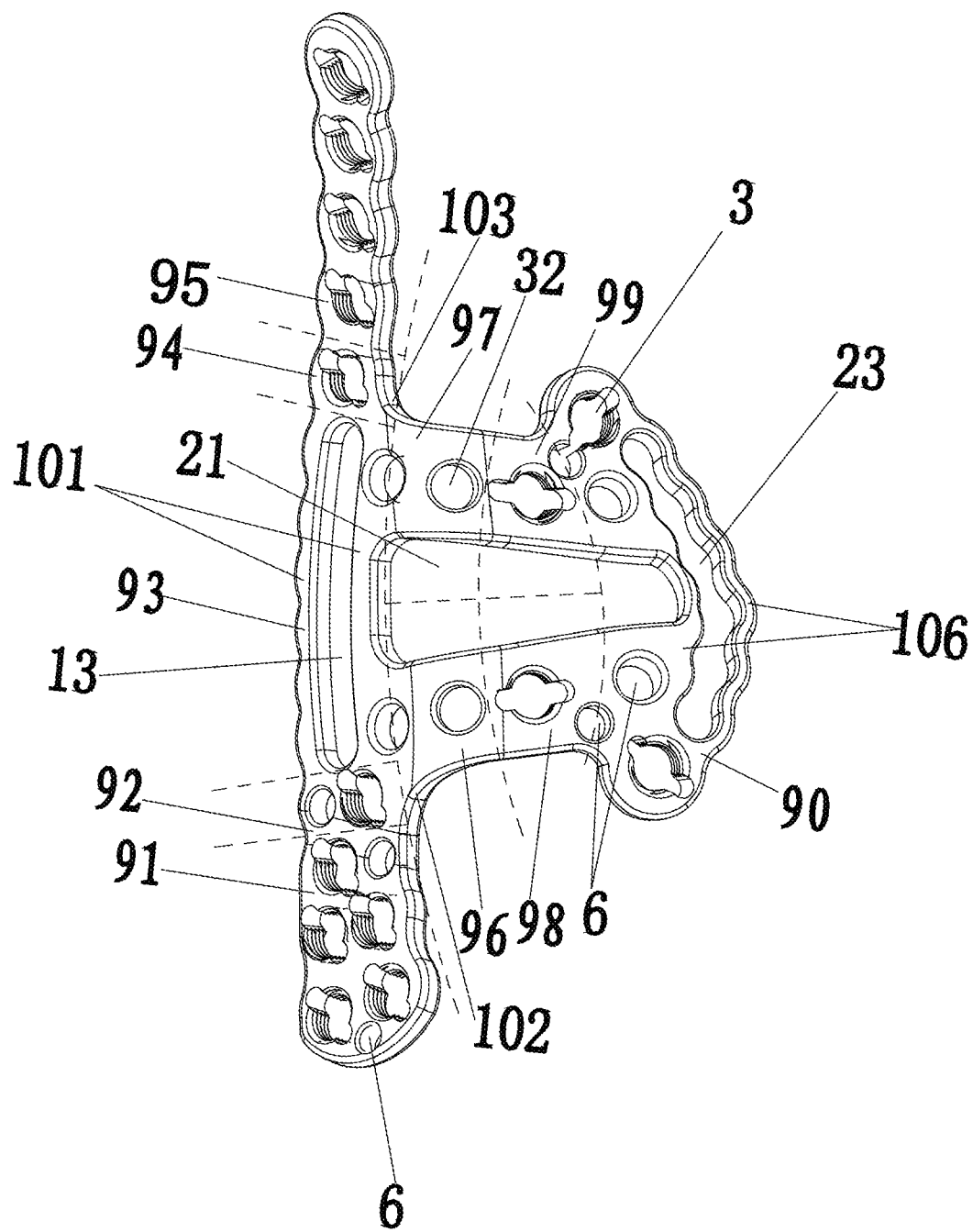
FIG. 5 is a structural schematic view of the second embodiment of the present invention.

In the embodiment, the screw holes 3 on the first fixation zone 91 are set in one or two rows. The eighth fixation zone 98 and the ninth fixation zone 99 are provided with 1 or 2 slot holes 3. Two fixing slots 3a set oppositely are provided on an inner wall of the slot hole 3. The fixing slots 3a are convenient for inserting the fixing feet 82, which stabilizes the screw to be inserted into the sleeve 8, and cushion the stress on the right plate after the screw is inserted tightly. The distribution of the screw holes 3 mentioned above complies with the load sharing principle and neutral principle. The right plate of the second embodiment shown in FIG. 5 is different from that of the first embodiment. A temporary positioning hole 6 is provided at an end of the first fixation zone 91 in the second embodiment for inserting kirschner wires and beneficial to the temporary positioning of the first fixation zone 91.

Figure 6:
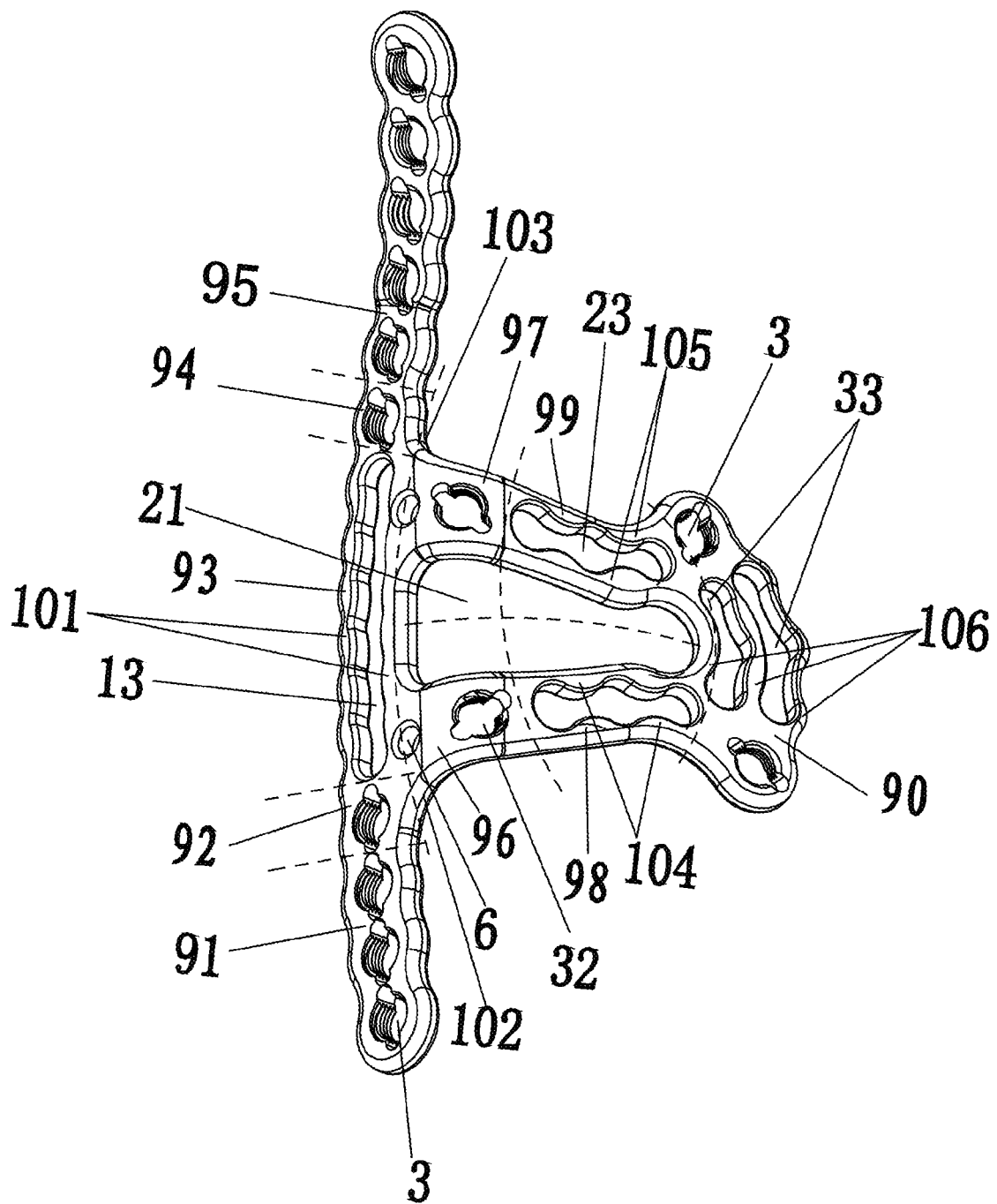
FIG. 6 is a structural schematic view of the third embodiment of the present invention.

As shown in FIG. 6, the right plate in the third embodiment is different from that in the first embodiment, which is applied to the patients with bigger bones, e.g. adults. The screw slots 3 on the first fixation zone 91 are set in 1 or 2 rows for the sake of strengthening the bolting area of the first fixation zone 91 and allowing the first fixation zone to cover more bone surface at the rear upper part of the acetabulum. There are five screw holes 3 in the fifth fixation zone 95 set in a row, which is beneficial to the fixation on thin superior ramus of pubis.

Figure 7:
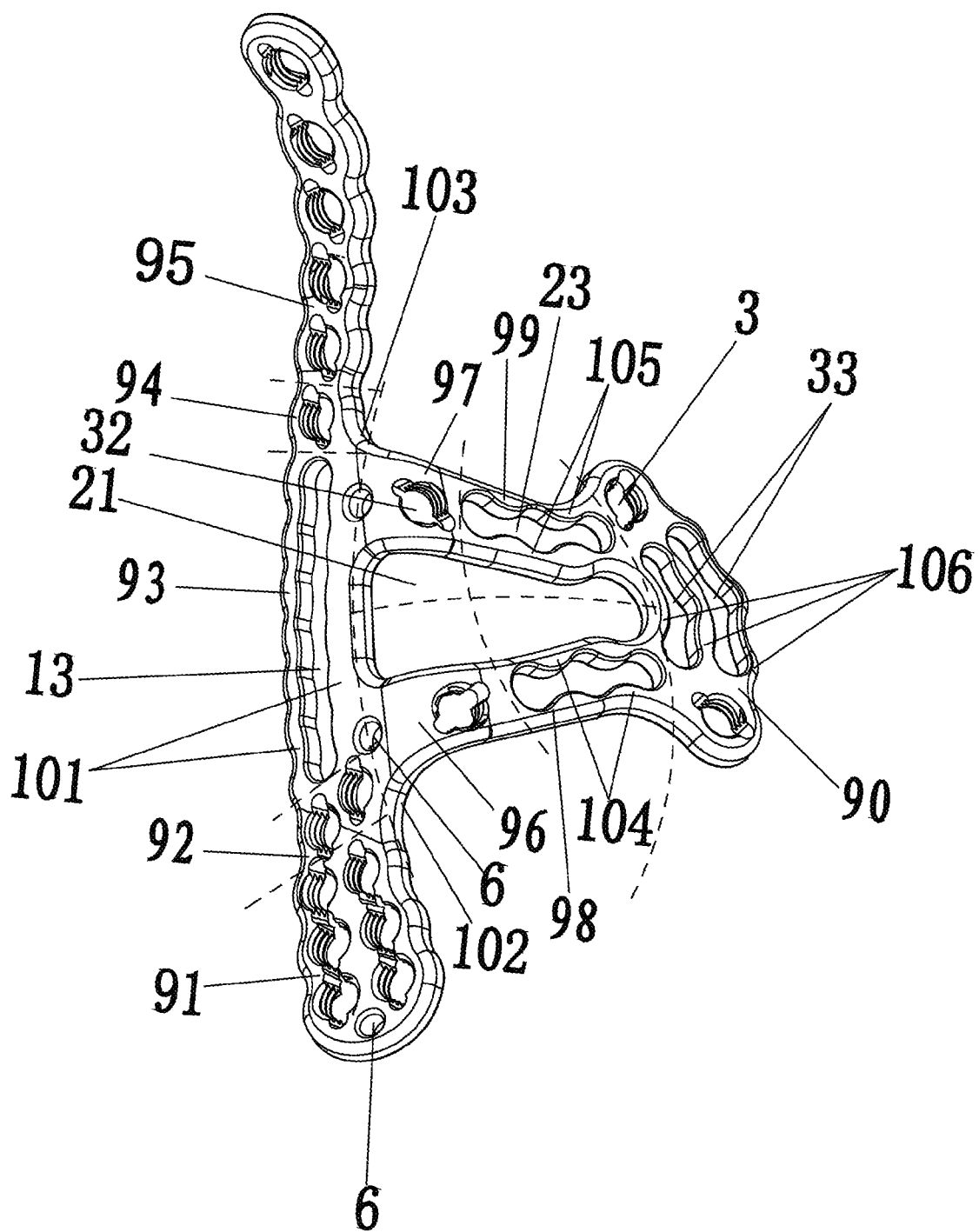
FIG. 7 is a structural schematic view of the fourth embodiment of the present invention.

Embodiment 4: as shown in FIG. 7, the right plate in the fourth embodiment is different from that in the third embodiment, wherein the vertical plate body is provided with 1-2 screw holes 3 at a place near the horizontal plate body, these screw holes being located in the sixth fixation zone 96 and the seventh fixation zone 97 respectively. Functioning as automatic reduction holes 32, the screw holes 3 can make the fracture fragments which protrude into a pelvic cavity a normal reduction, when inserting screws. There are 1-2 second sliding slots 33 in the area of the tenth fixation zone 90. The eighth fixation zone 98 and the ninth fixation zone 99 are provided with a third sliding slot 23, respectively. The plate bodies of the eighth and the ninth fixation zone 98 and 99 at two sides of the sliding slot 23 are respectively taken as a fourth stress bridge 104 and a fifth stress bridge 105. The fourth stress bridge 104 accords with the distribution of the bone trabecula of the internal pressure of the acetabulum, which conducts the pressure in the upper and rear to the ischial tuberosity, disperses the stress evenly, prevents concentrated stress after the fixation, and prevents steel plates from loosening and breaking. The fifth stress bridge 105 accords with the distribution of the bone trabecula of the internal pressure of the acetabulum, which conducts the pressure in the upper and rear to the ischial tuberosity, disperses the stress in the upper evenly.

Figure 8:
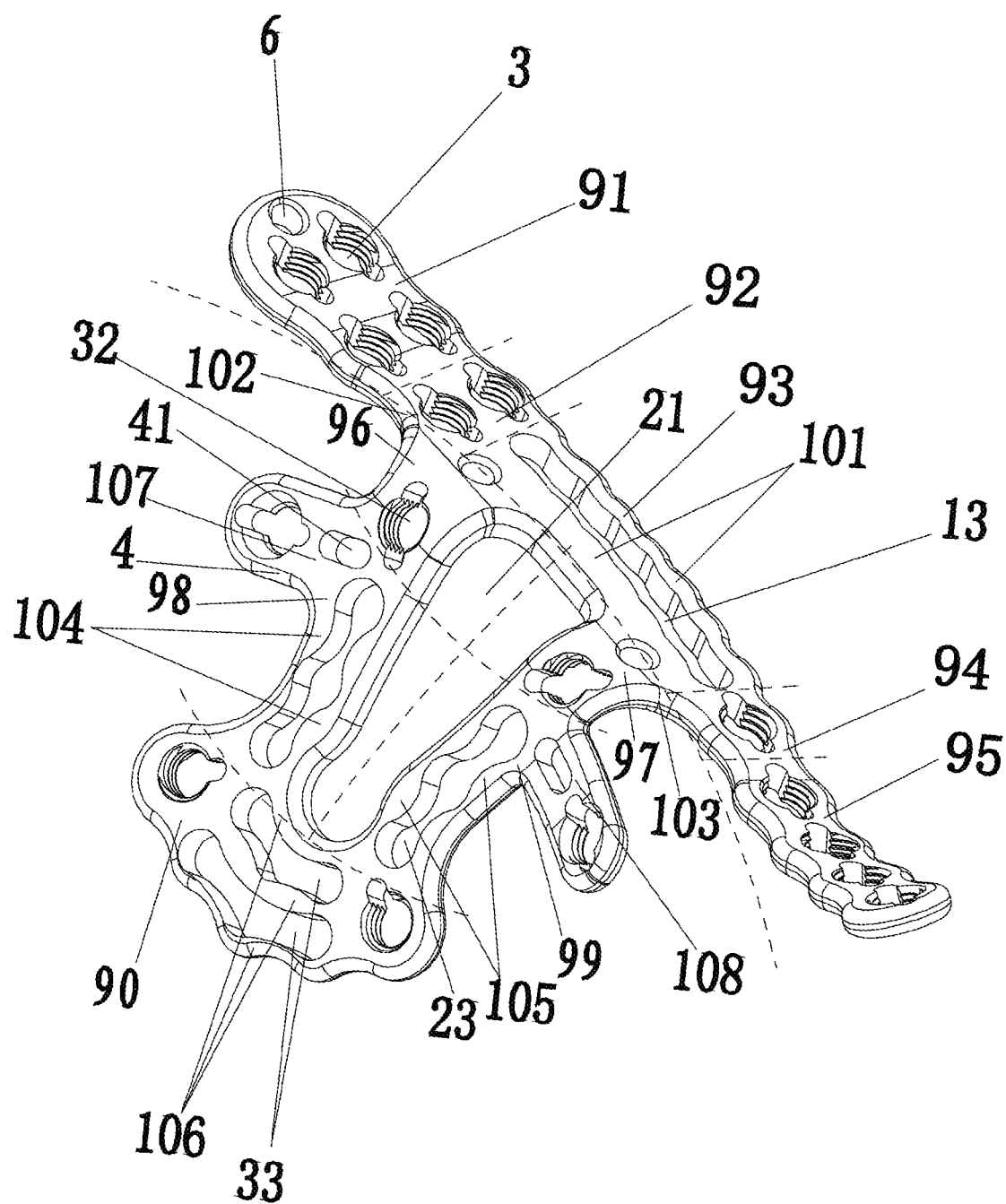
FIG. 8 is a structural schematic view of the fifth embodiment of the present invention.
Figure 9:
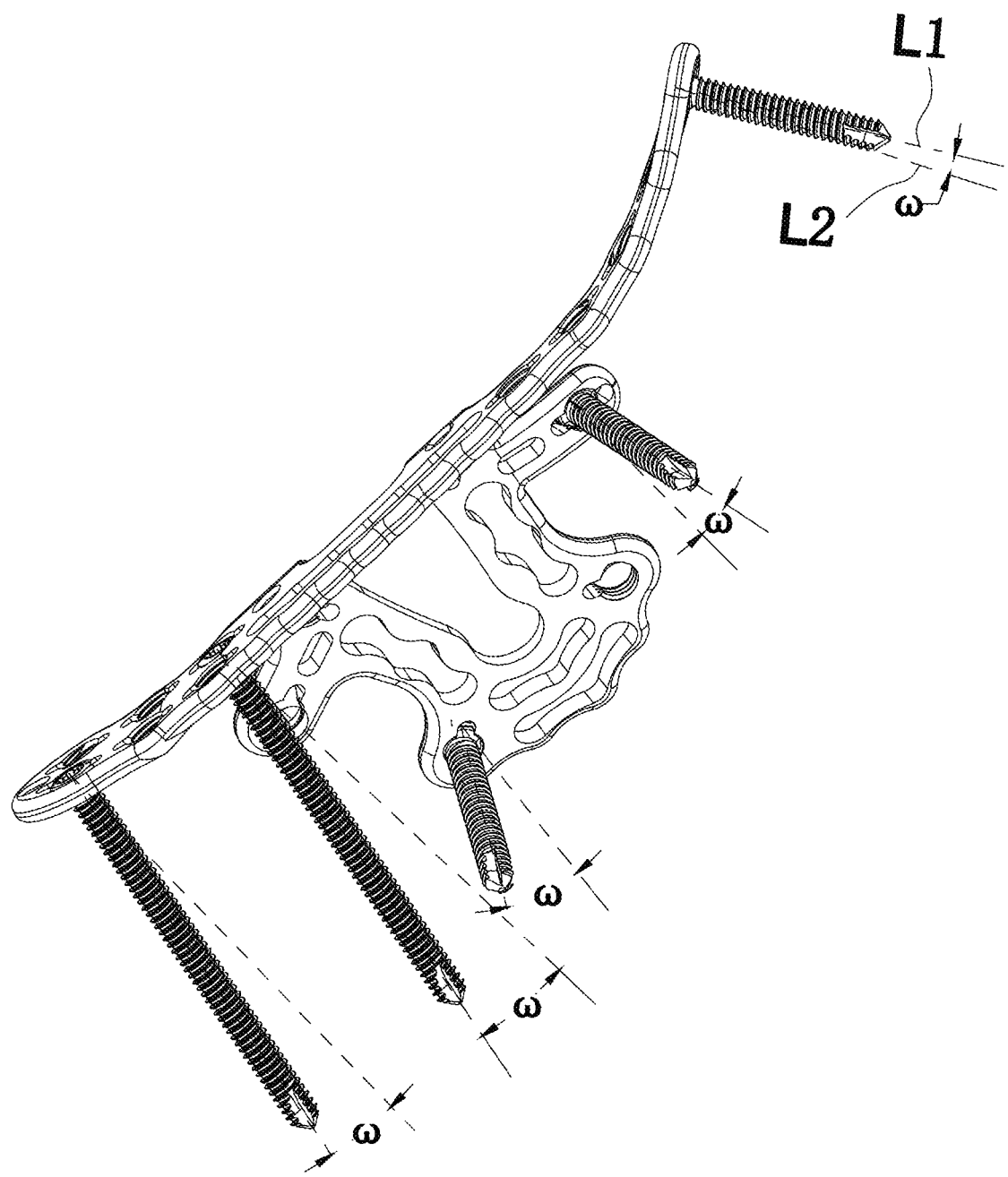
FIG. 9 is a schematic view showing the matching angle of the screw and the right plate in the fifth embodiment.
Figure 10:
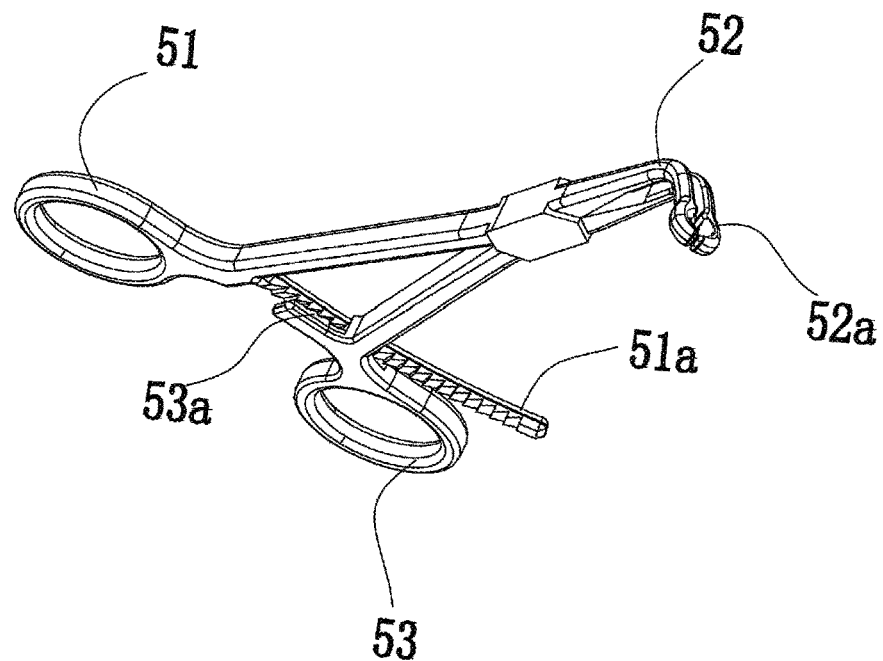
FIG. 10 is a structural schematic view of a pair of gripping pliers of the present invention.
Figure 11:
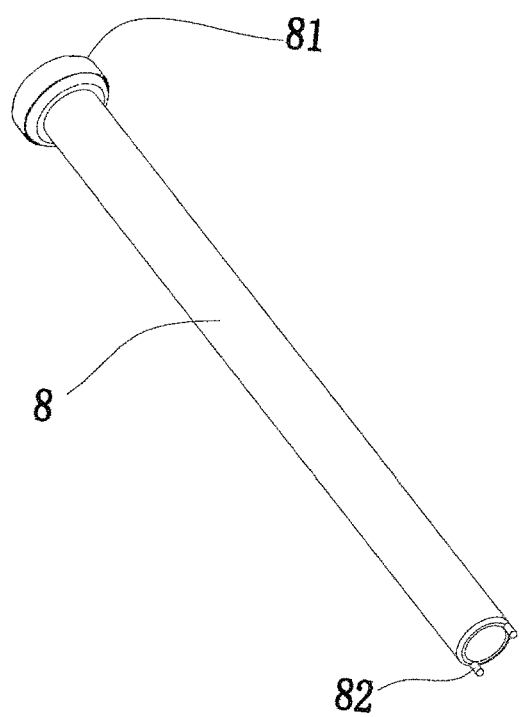
FIG. 11 is a structural schematic view showing a screw being inserted into a sleeve in the present invention.

Embodiment 5: as shown in FIG. 8, the right plate in the fifth embodiment is different from that in the third embodiment. In the fifth embodiment, a temporary positioning hole 6 is provided at an end of the first fixation zone 91 for the use of temporarily positioning kirschner wires. Each of the eighth fixation zone 98 and the ninth fixation zone 99 extends outward and forms a fixed arm 4, which matches the anatomic shape of the medial acetabulum. Each fixed arm 4 is provided with a screw hole 3 and a fourth sliding slot 41.

A length of the fourth sliding slot 41 is 3.0 mm to 6.0 mm, a width thereof is 2.2 mm to 3.5 mm, for fixing kirschner wires initially and thus allowing the right plate to adjust positions in no slipping scenarios, and ensuring that the right plate is positioned in a best position. Two fixed arms 4 are bolted to the connecting area of the anterior/posterior rim and the anterior/posterior column of the internal quadrilateral area of the acetabulum respectively, which is for the very severe shattered fractures in the quadrilateral area of the acetabulum or with pelvic fractures. The plate bodies of the eighth and the ninth fixation zone at two sides of the fourth sliding slot 41 are respectively taken as a seventh stress bridge 107 and an eighth stress bridge 108. The seventh and the eighth stress bridge is beneficial to conducting and dispersing the horizontal pressure stress, preventing over concentrated stress, and preventing embedded steel plates and screws from breakage.

The right plate in the fifth embodiment is applicable to the patients with bigger bone model and with fractures at acetabular posterior column, acetabular posterior wall, acetabular anterior column, or acetabular anterior wall.

An auxiliary apparatus of the anatomic self-locking plate for medial acetabulum comprises a locking sleeve, a screw placing sleeve 8 and a pair of gripping pliers, wherein the locking sleeve is provided with a first handle on a top thereof; the first handle is provided with skidproof grains on a periphery thereof and with positioning external threads 72 at an end thereof, the positioning external threads are engaged with internal threads of the screw hole of the right plate fittingly for leading a drill to drill directionally in order to pre-drill a safe screw pathway; the locking sleeve can accommodate the drill that matches the pore diameter of the screw pathway. A second handle 81 is provided on a top of the screw placing sleeve 8, with skidproof grains set on a periphery thereof. The second handle has one to two fixing feet 82 fittingly connected with the fixing slot 3a of the right plate. An adjustable angle of the sleeve and the right plate is set between 0° to 25° in order to ensure that the screw can be screwed at safe preset angle. The pair of gripping pliers is adapted for a right hand to hold, comprising a left finger circle 53, a right finger circle 51 and a gripping body 52. The left finger circle 53 is provided with a stopping bulge 53a on a top thereof. The right finger circle 51 extends along a direction of the stopping bulge 53a and forms a sawtooth bar 51a. The sawtooth bar is engaged with the stopping bulge 53a. Every time when the left finger circle 53 and the right finger circle 51 are clamped toward each other, the sawtooth bar 51a can be engaged on the stopping bulge 53a, thereby ensuring the pair of gripping pliers to hold objects firmly and prevent the right plate from slipping. The end of the gripping body expands and forms an annual gripping head 52a, which is able to hold cylindrical objects, in addition, which is provided with skidproof grains inside to increase the holding friction.

A method for installing an anatomic self-locking plate for medial acetabulum, comprises steps of: first, putting a first fixation zone 91 on an upper rear part of an acetabulum, i.e., a block area where an arcuate line part of a posterior column of the acetabulum inside a pelvis extends backward to a sacroiliac joint, wherein directions of screw holes 3 within the block area all point towards a posterior wall and posterior column of the acetabulum; next, fixing the posterior wall and posterior column area and making the area have a 0°-20° of inclining angle relative to a surface of the first fixation zone 91 to prevent the screws from getting into the joint; then fixing a rear half of a load bearing area on the acetabular dome with the screw holes 3 of a second fixation zone 92;

contacting a third fixation zone 93 with a part right above the acetabulum, fixing fractures in a fornix part right above the acetabular dome and acetabular anterior wall of the acetabulum, inserting Kirschner wires into the first sliding slot 13 to fix the right plate initially for allowing the right plate to adjust positions without slipping;

wherein the screws in the fourth fixation zone 94 point towards the anterior column and the anterior wall of the anterior lateral of the acetabulum, and have a 0°-20° of inclining angle relative to the surface of the 4th fixation zone 94 in order to prevent screws from getting into the joint; the front half of the load bearing area is fixed on the acetabular dome;

placing the fifth fixation zone 95 above the anterior column of the acetabulum, i.e., above the superior ramus of pubis, wherein the screw directions in this block area have a 0°-10° of inclining angle with respect to the surface of the fifth fixation zone, decreasing in sequence by a 3°-5° from the first hole adjacent to the third fixation zone for preventing the screws from getting into the joint; then, fixing the first half part of the loading bear area of the acetabular dome with the screw holes in the fourth fixation zone 94, and fixing the superior ramus of pubis of the anterior column of the acetabulum by using the remaining screw holes near the free end;

screwing the eighth fixation zone 98 to ½ of the upper-middle part of the posterior column of the acetabulum; screwing the ninth fixation zone 99 to ½ of the upper-middle part of the anterior column of the acetabulum; screwing the tenth fixation zone 90 to the lower-middle part of the quadrilateral area of the medial acetabulum; and the automatic reduction hole 32 making the fracture fragments which protrude into a pelvic cavity a normal reduction, when inserting screws.

The objectives of the present invention have been fully and effectively accomplished. Its embodiments have been shown and described for the purpose of illustrating the functional and structural principles of the present invention and is subject to change without departure from such principles. Therefore, this invention includes all modifications encompassed within the spirit and scope of the following claims.

What is claimed is:

1. A general anatomic self-locking plate for medial acetabulum comprising a horizontal plate body and a vertical plate body, wherein:
the horizontal plate body and the vertical plate body form a T shape;
the horizontal plate body comprises a first fixation zone, a second fixation zone, a third fixation zone, a fourth fixation zone and a fifth fixation zone connected with each other in sequence, and the vertical plate body is connected with the third fixation zone;
the vertical plate body comprises a sixth fixation zone, a seventh fixation zone, an eighth fixation zone, a ninth fixation zone and a tenth fixation zone, wherein: a through-hole is provided on the vertical plate body along a length direction thereof, provided between the sixth fixation zone and the seventh fixation zone and provided between the eighth fixation zone and the ninth fixation zone; the third fixation zone, the sixth fixation zone and the eighth fixation zone are connected with each other in sequence, the third fixation zone, the seventh fixation zone and the ninth fixation zone are connected with each other in sequence;

the tenth fixation zone is located at a free end of the vertical plate body for matching an anatomic shape of the medical acetabulum;
a first sliding slot is provided along a length direction of the third fixation zone, a second sliding slot is provided along a width direction of the tenth fixation zone, a portion of the third fixation zone at two sides of the first sliding slot defines a first stress bridge, a portion of the tenth fixation zone at two sides of the second sliding slot defines a sixth stress bridge; an arched junction of the horizontal plate body and the sixth fixation zone defines a second stress bridge; an arched junction of the horizontal plate body and the seventh fixation zone defines a third stress bridge;
the first, second, third, fourth, fifth, eighth, ninth and tenth fixation zones are all provided with locking screw holes;
a rim of the self-locking plate has a smooth shape.

2. The general anatomic self-locking plate for medial acetabulum, as recited in claim 1, wherein: an angle $\gamma_1$ between a free end of the first fixation zone and the third fixation zone is in a range of 5°-18°; an angle $\gamma_2$ between a free end of the fifth fixation zone and the third fixation zone is in a range of 0°-10°; an intersection angle $\varepsilon$ formed by a central axis of the vertical plate body and a central axis of the third fixation zone is in a range of 95°-105°;
an angle $\alpha_1$ of the eighth fixation zone and the first fixation zone is in a range of 105°-120°, an angle $\beta_1$ of a central axis of the eighth fixation zone and the third fixation zone is in a range of 105°-120°;
an angle $\alpha_2$ of the ninth fixation zone and the fifth fixation zone is in a range of 99°-105°, an angle $\beta_2$ of a central axis of the ninth fixation zone and the third fixation zone is in a range of 90°-105°;
a length of the first sliding slot is in a range of 25.0 mm-50.0 mm and a width thereof is in a range of 3.0 mm-8.0 mm, a length of the second sliding slot is in a range of 3.0 mm-10.0 mm and a width thereof is in a range of 2.2 mm-3.5 mm;
an angle $\omega$ formed by a central axis of one of the screw holes and a normal line of an end surface of the one of the screw holes is in a range of 0°-20°.

3. The general anatomic self-locking plate for medial acetabulum, as recited in claim 2, wherein a temporary positioning hole for using Kirschner wires is provided in the horizontal plate body of the self-locking plate; the sixth fixation zone and the seventh fixation zone are provided with 1-2 automatic reset holes, respectively.

4. The general anatomic self-locking plate for medial acetabulum, as recited in claim 1, wherein:
an inner surface of the horizontal plate body in each of the first, second, fourth and fifth fixation zones defines upper and lower end surfaces of each of the screw holes in the each of the first, second, fourth and fifth fixation zones;
the upper end surfaces of the screw holes in the first fixation zone, the second fixation zone, the fourth fixation zone and the fifth fixation zone are closer to a central axis of the third fixation zone than the lower end surfaces thereof;
an inner surface of the vertical plate body in the sixth fixation zone and the seventh fixation zone defines upper and lower end surfaces of the screw holes in the sixth fixation zone and the seventh fixation zone;

the upper end surfaces of the screw holes in the sixth fixation zone and the seventh fixation zone are closer to the through-hole than the lower end surfaces thereof.

* * * * *